United States Patent [19]

Cooper et al.

[11] Patent Number: 4,754,142
[45] Date of Patent: Jun. 28, 1988

[54] GAS DETECTOR AND MINING MACHINE

[75] Inventors: Alan J. Cooper, Wingerworth; Ronald G. Coombes, Welwyn Garden City, both of England

[73] Assignee: Pitcraft Summit Limited, Hoyland Nether, England

[21] Appl. No.: 930,650

[22] Filed: Nov. 13, 1986

[30] Foreign Application Priority Data

Nov. 20, 1985 [GB] United Kingdom ................ 8528549

[51] Int. Cl.$^4$ ................................................ G01J 1/00
[52] U.S. Cl. ..................................... 250/343; 250/253
[58] Field of Search ................ 250/343, 253, 338 R, 250/349; 73/23

[56] References Cited

U.S. PATENT DOCUMENTS

| | | | |
|---|---|---|---|
| 3,245,509 | 4/1966 | Larson | 250/338 R |
| 3,562,522 | 2/1971 | Cederstrand et al. | 250/343 |
| 3,593,023 | 7/1971 | Dodson et al. | 250/343 |
| 3,963,927 | 6/1976 | Bruce et al. | 250/343 |
| 4,485,666 | 12/1984 | Higgins et al. | 73/23 |

Primary Examiner—Janice A. Howell
Assistant Examiner—William F. Rauchholz
Attorney, Agent, or Firm—Trexler, Bushnell, Giangiorgi & Blackstone, Ltd.

[57] ABSTRACT

A gas detector (1) to detect a predetermined gas of interest within an air sample, the detector (1) comprising a sampling tube (12), an infra-red radiation source (13) located at one end of the tube (12), an infrared sensing means (17) located at the other end of the tube, an optical filter (16) appropriate to the gas of interest located in the infra-red radiation beam, either adjacent the infra-red source (13), or adjacent the infra-red sensing means (17), an air sample inlet located at or towards one end of the tube (12) and an air sample outlet located at or towards the other end of the tube (12), with the detector (1) capable of emitting an electrical signal or a changed electrical signal in accordance with whether the gas of interest is or is not detected, a pure, reference gas source (26-30) and valve means (31, 32) to control admission of the reference gas to the sampling tube (12) at prescribed intervals of time.

23 Claims, 5 Drawing Sheets

GAS DETECTOR AND MINING MACHINE

This invention relates firstly to a gas detector particularly, though not exclusively for detecting a gas or gasses of interest e.g., hydrocarbon gases such as methane, in an air sample, and secondly to a mining machine provided with such a gas detector.

Portable gas detectors, operating on a catalytic basis, are known, and are used extensively in coal mines for methane detection, but such gas detectors have a relatively slow response time, of the order of 20 seconds, and require re-calibration at regular intervals, e.g. every two weeks, in British coal mines. If a more rapid response is required e.g. for use in halting machinery such as a coal cutting machine, upon methane being detected at or above the prescribed limit of 1.25%, then one must move to a gas detector operating on an infra-red basis, but whilst rapid response is achievable with such gas detectors, they have a tendency to deflect from calibration relatively quickly, and consequently known infra-red gas detectors usually embody some calibration checking/resetting means for regular use. In practice, a known infra-red gas detector comprises an air sampling tube, with an infra-red source, located at one end of the tube, and with infra-red radiation being projected into the tube, with an infra-red sensing means located at the other end of the tube and with air to be sampled passed into, along, and out of, the tube. An optical filter is placed in the infra-red beam, inside the air sampling tube, either adjacent the infra-red source, or adjacent the infra-red sensing means. The characteristics of the filter are selected in accordance with the gas of interest. Basically, the arrangement is such that the infra-red sensing means emits no electrical signal, or an electrical signal at a non-alarm level, when the gas of interest is not sensed, or is not sensed above a prescribed threshold, resulting from the infra-red radiation having a "clear" passage to the sensing means but when the gas of interest is present at some level in the air sampling tube, the infra-red radiation being received by the sensing means is attenuated and, above a predetermined level, e.g. 1.25% for methane, the loss or reduced sensing of infra-red radiation at the sensing means results in the latter emitting an electrical signal or an alarm electrical signal. The expected loss of calibration accuracy—which is due to example to contaminants either on the mirror finished, gold plated inner surface of the air sampling tube, or to degradation of the infra-red source, to degradation of the filter and/or to degradation of the infra-red radiation detector—is corrected for example by incorporating a sealed, reference tube with windows at each end, which is rotated from a storage position to an active position between the infra-red source and the infra-red sensing means, for re-calibration purposes e.g. at 100 times per minute, with the air sampling tube simultaneously rotated to a storage position. The arrangement is such that the sampling tube and reference tube are located at the same radial distances from the axis of rotation of a tube carrier, the latter being drivable by an electric motor and consequently requiring connection to a source of electrical power. The above arrangement is satisfactory in use but requires a second tube (the reference tube), a carrier located in bearings, a drive motor and a power source, all of which result in substantial manufacturing and maintenance costs, and are susceptable to failure.

According to a first aspect of the present invention, there is provided a gas detector to detect a pre-determined gas of interest within an air sample, the detector comprising an air sampling tube, an infra-red radiation source located at one end of the air sampling tube, an infra-red sensing means located at the other end of the air sampling tube, an optical filter appropriate to the gas of interest located in the infra-red radiation beam, either adjacent the infra-red source, or adjacent the infra-red sensing means, an air sample inlet located at or towards one end of the air sampling tube and an air sample outlet located at or towards the other end of the air sampling tube, with the detector capable of emitting an electrical signal or a changed electrical signal in accordance with whether the gas of interest is detected, or is detected above a prescribed threshold, a pure, reference gas source, and valve means to control admission of the reference gas to the air sampling tube at prescribed intervals of time.

Thus, the detector in accordance with the first aspect of invention requires the air sampling tube to effect the functions of both a sampling tube and a reference tube, thereby dispensing with the need of prior art proposals for a second, reference tube, a carrier, a drive motor and its power source, and also dispensing with the need for regular calibration.

According to a second aspect of the present invention, there is provided a mining machine connected to a gas detector as defined above.

The gas detector may be "on board" and hence carried by the machine, or may be remote from the machine but connected thereto and to the associated mining telemetry system.

The machine may be of the shearer type or alternatively of the roadheader type, with operation of the machine stopped automatically, e.g. by de-clutching a transmission to a rotary cutting head of the machine, upon an electrical signal, or changed electrical signal, being emitted by the gas detector upon detection of the gas of interest above a prescribed threshold, which gas of interest, if coal mining were involved, would be methane ($CH_4$), which is invariably present and can be tolerated to some small extent e.g. <1.25%, but which is unacceptable at least in British coal mines, above the 1.25% prescribed threshold.

The machine in accordance with the second aspect may advantageously be shut down rapidly, e.g. within 1 second of methane, above a prescribed threshold being sensed by the sensor. This is a substantial safety benefit. It will be appreciated that the virtual instantaneous stopping of rotation of a rotary mineral cutting head prevents any or all sparking or heat generation at the head upon an alarm signal being emitted. No brake for the cutting head is necessary because if rotating in the cut, the mineral acts as a brake, whilst if rotating out of the cut it is not generating sparks or heat. Tests have shown that the detector in accordance with the invention satisfactorily operates sampling 100 cc of air/minute, with a response time of 0.5 sec.

The reference gas is for example $CO_2$, conveniently supplied from a cylinder, and it may be admitted to, and passed through, the air sampling tube automatically, at prescribed intervals of time e.g., every ten minutes, conveniently under the control of a timing device, preferably of an electronic kind and preferably of an adjustable kind, to suit particular requirements. In order to ascertain that the $CO_2$ cylinder is not exhausted and is functioning properly, a reference gas pressure switch is preferably incorporated in a supply line from the $CO_2$ cylinder.

A valve may be used to control admission of air samples or, at the prescribed time intervals, pure reference gas to the air sampling tube; and a solenoid operated valve is suitable for this purpose the valve being operable by the timing device.

With $CO_2$ at a super atmospheric pressure it will readily course along the air sampling tube when admitted to the air sampling tube by the solenoid valve. The air to be sampled however is usually at atmospheric pressure, e.g. being mine air potentially containing methane, and consequently, needs to be forced or drawn through the air sampling tube by air pumping means. Such means may be constituted for example a venturi and an associated water spray nozzle, water being sprayed along the venturi tube to induce an air flow along the venturi tube. The air sample exit from the air sampling tube is conveniently connected to the sub-atmospheric pressure zone of the venturi, thereby inducing sample air flow through the air sampling tube. Alternatively, it may be more convenient to employ a small, e.g. electrically driven, air pump. The air sample inlet to the air sampling tube is in practice located in a suspected zone of location of the gas of interest e.g., methane. As mine air is dust laden, it is clearly desirable to locate an air filter e.g., a porous, sintered-metal filter in the air sample inlet. As another safety feature to establish that the gas detector is itself not malfunctioning, e.g. by the air sample inlet or inlet filter being blocked, the air sample outlet is preferably provided with an air flow detector. This may be of the mass flow meter kind. Such a meter contains two heater resistance thermometers which are used to measure air/gas flow. A bridge circuit senses the temperature differential and develops a linear output signal.

As it has been determined that barometric pressure changes affect the accuracy of the gas detector, it is preferred to provide the gas detector with a barometric pressure compensating device such as a pressure capsule capable of emitting a correcting electrical signal, so that the depth in a mine at which the gas detector is located, or the atmospheric conditions, are of no consequence.

With regard to the second aspect of the invention and a coal cutting machine in particular, methane release, and hence concentration, will generally be at a maximum in the vicinity of the rotary cutting head(s). It is therefore preferred to provide the mining machine in accordance with the second aspect of the invention with at least one gas detector in accordance with the first aspect in the vicinity of the rotary cutting head of the mining machine. As a rotary cutting head of the spiral vane kind is conventionally provided with a mineral loading cowl, a gas detector may be mounted on the cowl, to sample air from the region between the cowl and the cutting head. Alternatively or in addition, a gas detector may be mounted on a ranging arm which conventionally supports the rotary cutting head, to sample air from the region of the machine-side end of the rotary cutting head. In this region it is particularly advantageous to sample air entering the conventionally-provided hollow shaft of the rotary cutting head, which hollow shaft is used to achieve a preferred air circulation and ventilation route. Yet again a circular shield may be located in close proximity to the machine-side end of the shaft to encourage air to exit the rotary cutting head, or the cut, in a preferred direction, with a gas detector sampling this exiting air.

Apart from methane release at the rotary cutting head, ventilation air is conventionally coursed along a coal face from one end to the other, and it is not unknown for a "plug" of methane to be released from strata upstream and to travel towards an operating machine, at the rotary cutting head of which machine methane, if present, is within the prescribed limits. It is therefore preferred to mount a further gas detector at an "upstream" end of the machine to detect any "plugs" of methane etc., advancing toward the mining machine with the normal, ventilating air flow. Such a gas detector would be wired into the normal electric/electronic controls of the machine, to be capable of effecting machine cut-out and thus to act as another safety feature.

The invention will now be described in greater detail, by way of examples, with reference to the accompanying drawings, in which.

The gas detector 1 comprises a outer casing 2, through which casing passes a primary air sample circuit 3, in the form of tubing, to remove air, via an air filter 4 at an inlet end of the circuit 3, from a coal mine atmosphere for example, the air flow direction along the circuit 3 to an open, exit end 5 being shown by the arrows 6, and the air flow through the circuit being effected by means described later with respect to FIGS. 2 to 7.

Figure 1:
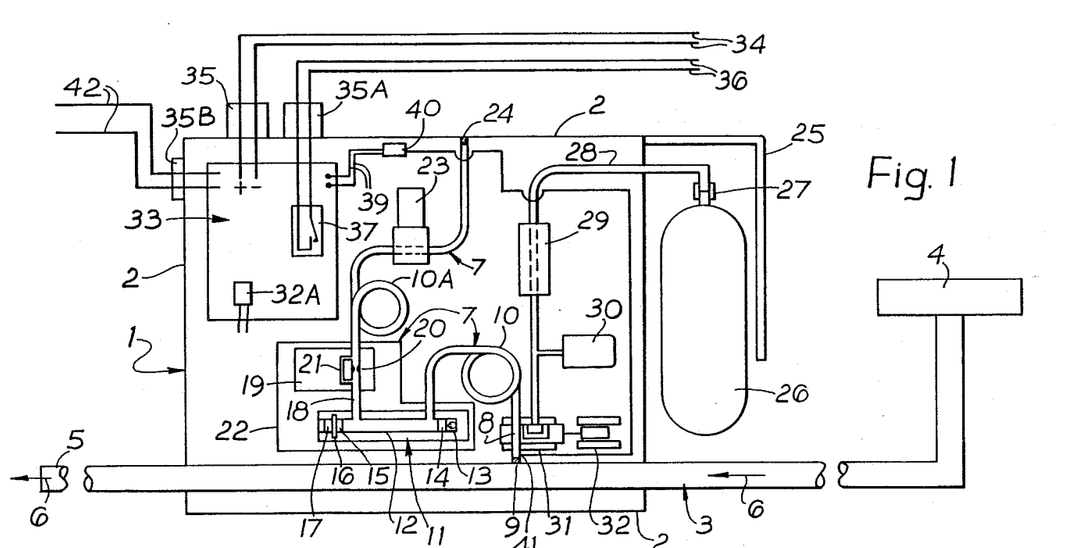
FIG. 1 is a schematic view of a gas detector in accordance with the present invention.

A secondary air sample circuit 7 is adapted to extract air from the primary air sample circuit 3, the secondary circuit 7 comprising an inlet 8 protected by a porous, sintered-metal filter 9, extending to a compliant loop 10 to allow for anti-vibration mountings, and beyond the loop 10 to one, (inlet) end of an infra-red detector cell assembly 11 comprising an air sampling tube 12. At the inlet end, the air sampling tube 12 is also provided with an infra-red radiation source 13 and a transparency 14 to protect the source 13, while the other, (outlet) end of the air sampling tube 12 is provided with a transparency 15 to protect an optical filter 16, and an infra-red sensing means 17. The air sample passes along the air sampling tube 12 and exits via an outlet 18 in the form of tubing which passes through a mass flow meter 19 which incorporates a flow restrictor 20 and a sensing loop 21, the detector assembly 11 and the mass flow meter 19 being mounted on a common anti-vibration table 22, and beyond the mass flow meter 19, the tubing is coiled into a second compliant loop 10A beyond which is an air pump 23 to induce air flow through the secondary circuit 7, air existing from the casing 2 via a porous, sintered-metal filter 24.

The casing 2 carries a guard 25 for a cylinder 26 containing a pure reference gas ($CO_2$), the cylinder 26 having a coupling 27 from which leads a supply line 28 passing into the casing 2 to a $CO_2$ pressure regulator 29, beyond which is a $CO_2$ pressure switch 30, a valve 31, and a solenoid 32, the valve 31 being capable of admitting $CO_2$ to the secondary sample circuit 7 ahead of the loop 10, under control of an electronic timer 32A.

Also, located within the casing 2 is an electronic circuit 33, having a power supply leads indicated at 34 and passing into the casing 2 via a cable connection 35, while leads 36 extend from the casing 2 to control a conventional pilot electrical circuit of an associated coal mining machine 38 (not shown in FIG. 1), the leads being introduced into the casing 2 via a similar cable connector 35A and extending to a tripping relay 37. Also forming part of the circuit 33 and within the casing 2 are leads 39 from a barometric pressure compensating device 40, a sampling port of which is connected at 41 to the sampling circuit at a position located between the entry sintered filter 9 and the valve 31. Finally, from the circuit 33 extend leads 42, passing through the casing 2 via a cable connector 35B, to the conventionally provided mine data transmission, or data collection systems.

Figure 1A:
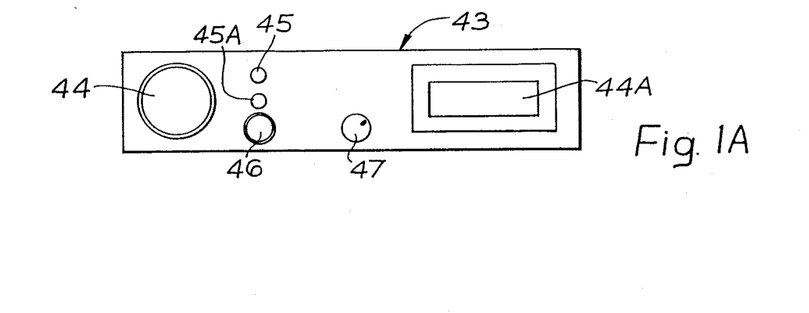
FIG. 1A is a display panel of the gas detector of FIG. 1.

Display panel 43 of FIG. 1A comprises a methane alarm lamp 44, L.E.D. warning lamps 45 and 45A respectively for low air flow and low $CO_2$ pressure, a switch 46 for text/reset, a tamperproof access 47 for barometric adjustment, and an L.C.D. 44A to display the % volume of $CH_4$ detected within the air samples.

In FIGS. 2 to 7, the longwall, mineral mining machine 38 is shown located alongside a face 48 of a coal seam 49, the machine 38 hauling itself from right to left and being mounted on, and guided by, an armoured scraper chain conveyor (not shown) seated on a mine floor 50. The machine 38 comprises a motor module 51 housing an electric motor (not shown) having a first output shaft to a machine haulage unit 52 comprising a drive sprocket 53 adapted to engage a static rack bar or chain (not shown) associated with the conveyor. The electric motor has a secondary output shaft 54 to power, via a clutch 55 (to be described in detail later), a pick carrying, rotary cutting head 56 mounted on a ranging arm 57 for rotation about an axis 58, which arm 57 is pivotally attached to a gear-head 59 of the machine 38, and is arcuately displaceable about its pivot by a double-acting control ram (not shown), in the well known manner.

The cutting head 56 is provided with a hollow shaft 60 located co-axially with the axis of rotation 58, the hollow shaft 60 incorporating at least one water spray nozzle 61 connectable to a source of pressurized water, to produce water jet(s) 62 to induce a flow of air along the hollow shaft 60, for methane dilution purposes, the air-flow being from an inlet end 63 of the hollow shaft 60, remote from the mineral face 48, as indicated by arrows 64, to be discharged adjacent the mineral face 48 at an outlet end 65, as indicated by arrows 66. Additional air is sucked from the exit end 5 of the primary air sample circuit 3 by the exit end 5 being located within the hollow shaft 60, and hence is sucked through the gas detector 1, this additional air being indicated by arrow 67.

Figure 2:
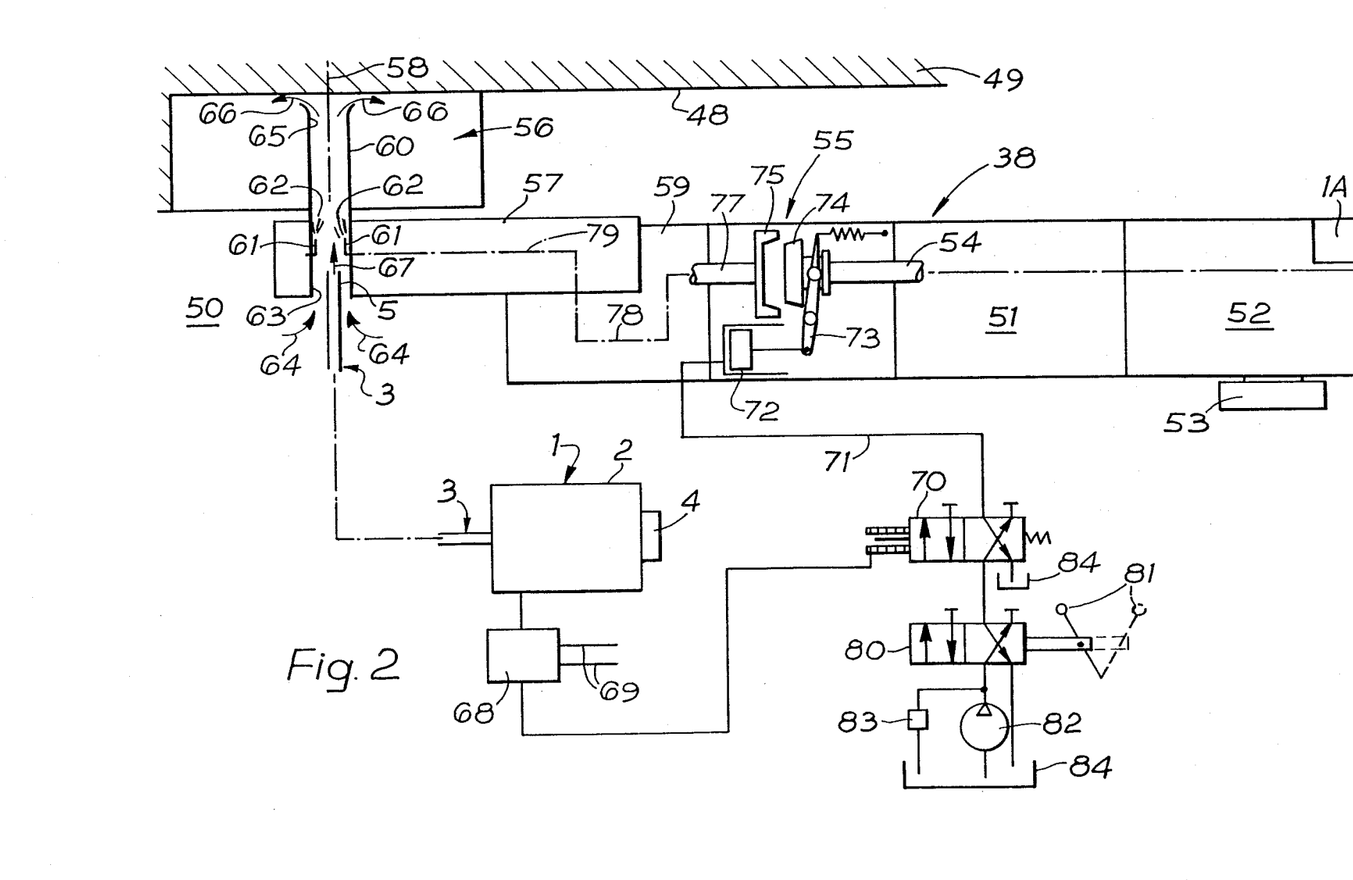
FIGS. 2 to 6 are schematic views of a shearer type mining machine in accordance with the second aspect of the present invention.

In the embodiment of FIG. 2, the gas detector 1 has an electrical output connected to an electrical relay 68, for example an intrinsically safe, flameproof interfacing relay, having an electrical power supply via leads 69 from a preferably intrinsically safe source (not shown), the relay 68 in turn being connected to a solenoid-operable control valve 70, in turn connected by a line 71 to an hydraulic actuator 72 adapted to pivot a clutch operating lever 73 to place engageable drive elements 74 and 75 of the clutch 55 into or out of driving engagement, the element 75 being attached to a drive shaft 77 to drive a speed-reducing transmission 78 contained within the gearhead 59, and transmission 79 contained within the ranging arm 57, to power the rotary cutting head 56. Connected in series with the solenoid-operable clutch control valve 70 is a manually-operable clutch control valve 80 having a manually operable lever 81. The valve 80 is in turn connected to an hydraulic pump 82 and a pressure relief valve 83, the valves 70, 80, pump 82 and relief valve 83 all being connected to tank 84.

The arrangement is such that with the electric motor of motor module 51 running, the machine operator appropriately displaces the operating lever 81 when it is desired to commence rotation of the rotary cutting head 56 and pressurised water is immediately supplied to spray nozzle(s) 61 to produce water jet(s) 62 to induce an air flow along the hollow shaft 60 which in turn sucks air through the primary air sampling circuit 3 and hence through the gas detector 1. However, because of the interposition of the valve 70 between the valve 80 and the hydraulic actuator 72, the clutch 55 is not immediately engaged, but remains in the position illustrated in FIGS. 2 and 5, until such time as the gas detector 1 detects no methane, or detects methane within prescribed limits, within its cell assembly 11, whereupon an electrical signal is passed to the relay 68, and in turn to the solenoid valve 70, permitting flow of hydraulic fluid to the hydraulic actuator 72, engagement of the clutch 55, and rotation of the cutting head 56. Thus, in the embodiment of FIG. 2, an active machine start-up system is employed, resulting in the prevention of engagement, or prevention of continued engagement, of the clutch 55, and hence rotation of the cutting head 56, until a signal indicating satisfactory gas of interest conditions within the cell assembly 11 has been emitted from the gas detector 1. After machine start-up, with the cutting head 56 rotating if the gas detector 1 should sense the gas of interest above a prescribed threshold, then another signal is emitted to the relay 68 to reverse the solenoid valve 70 with the result that the hydraulic actuator disengages the clutch 55, and hence rotation of the cutting head 56 of the machine 38 is automatically stopped. Also illustrated in FIG. 2 is the possibility of mounting a further gas detector 1A on board the machine 38 at an "upstream" end of the machine 38, to detect any "plugs" of methane, released from coal strata remote from the machine 38, and being advanced towards the machine 38 by the conventional flow of ventilating air along the face 48, from right to left of FIG. 2, with the gas detector 1A also wired, via a relay, to the solenoid valve 70.

Figure 3:
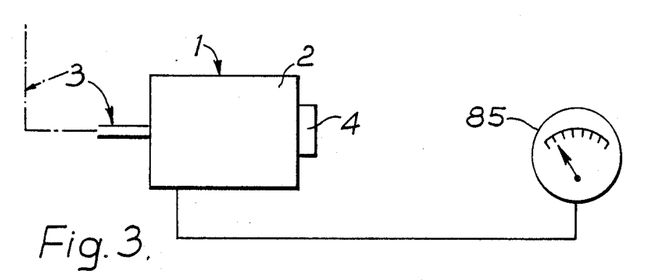
Figure 4:
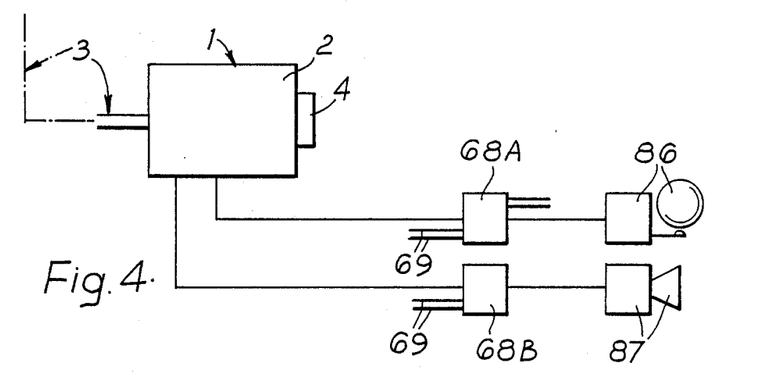

In the embodiment of FIGS. 3 and 4, a passive warning system is employed, in that output signals from the gas detector 1 are simply fed to a visual warning device, such as an analogue or digital readout 85 calibrated in units of % volume, and/or also fed via relays 68A and 68B to an audible warning device, as exemplified in FIG. 4, such device being in the form of a bell 86 or a horn 87.

Figure 5:
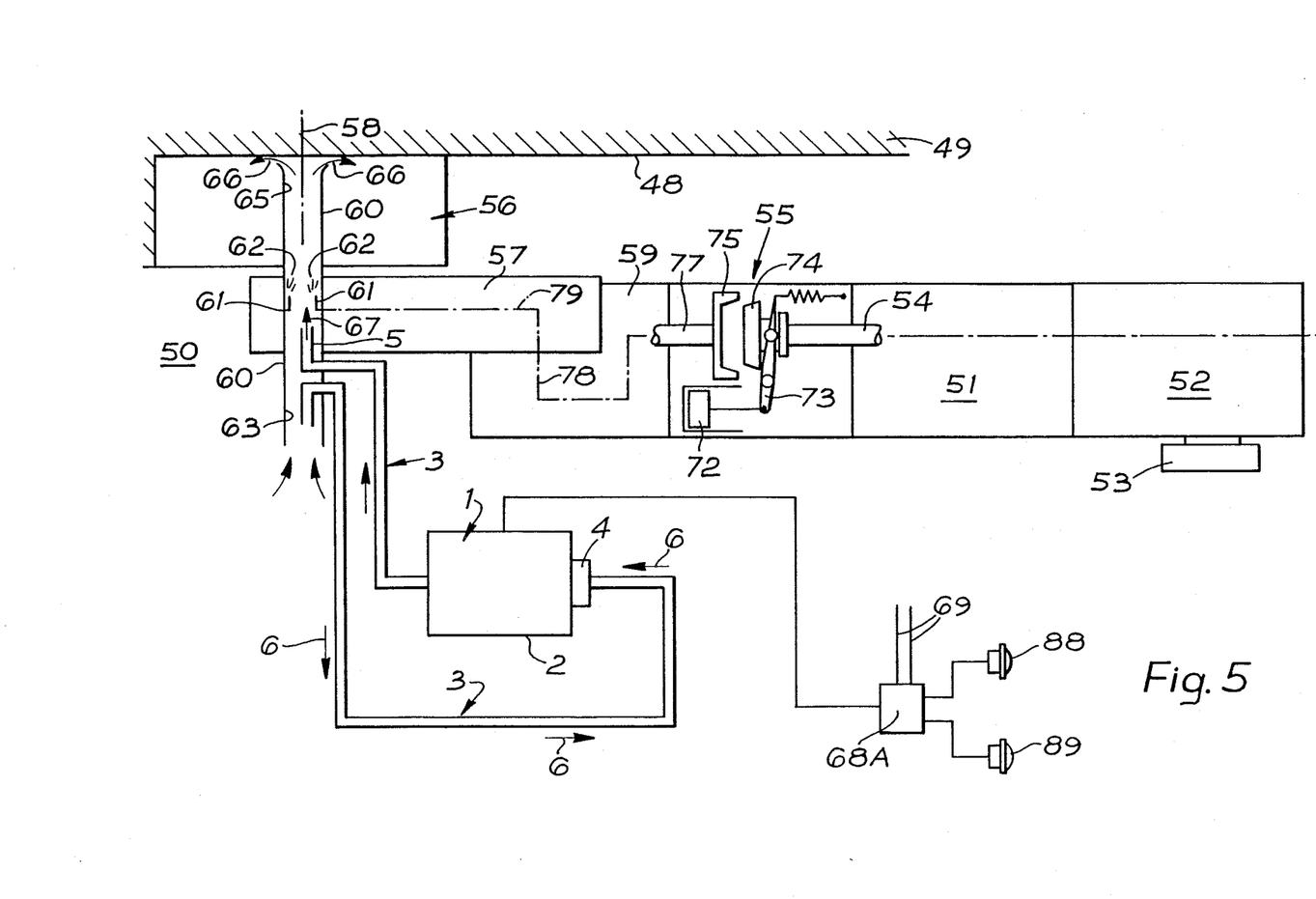

In the embodiment of FIG. 5, another passive system is indicated, in which the inlet end filter 4 of the primary air sample circuit 3 is located within the hollow shaft 60 and hence draws not ambient air, but air from within the hollow shaft 60. A relay 68A is connected to an alarm warning light 88 and a non-alarm indicator light 89.

Figure 6:
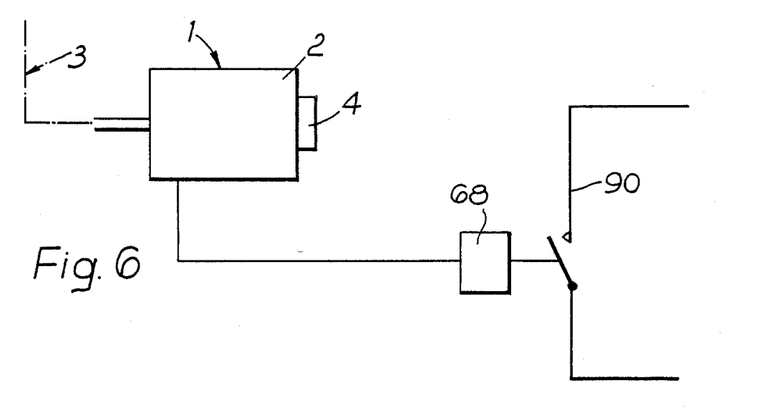

In the embodiment of FIG. 6 is illustrated another active system, with the output from relay 68 opening or closing a conventionally-provided pilot circuit 90 of the mining machine 38, to allow or prevent rotation of the cutting head 56.

Figure 7:
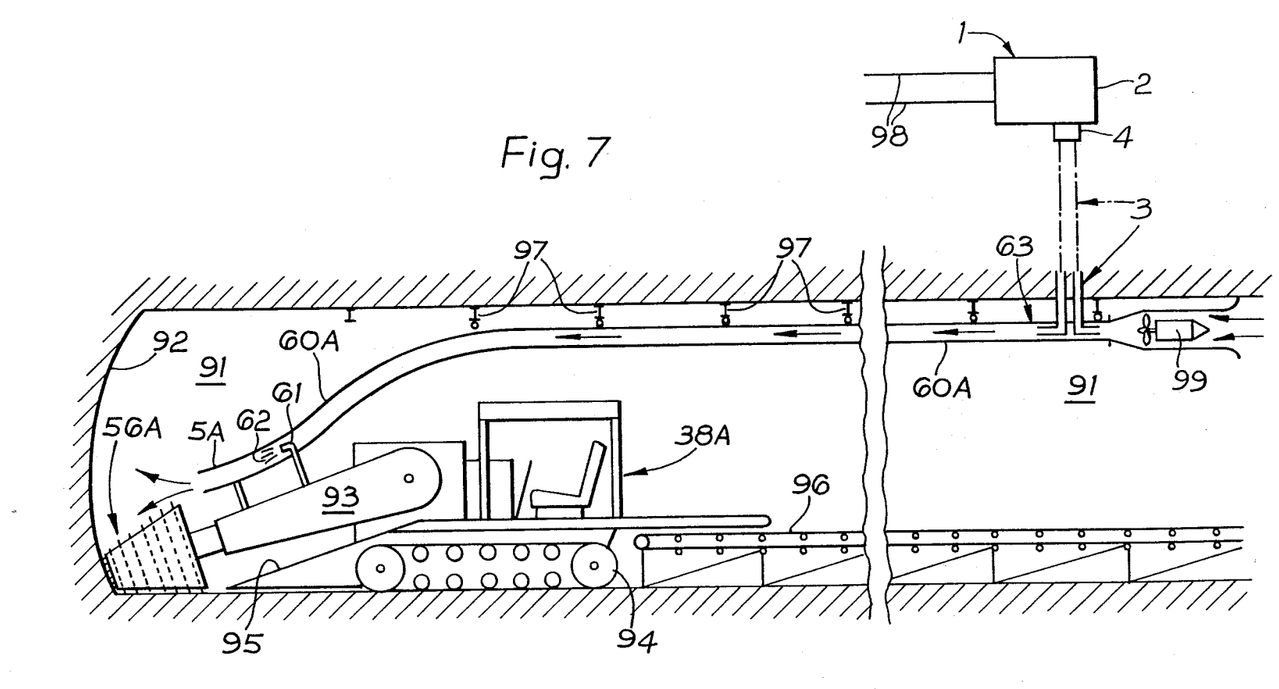
FIG. 7 is a schematic view of a roadheader type mining machine in accordance with the second aspect of the present invention.

In the embodiment of FIG. 7 a roadheader type mineral cutting machine 38A is illustrated, for the driving of a tunnel or roadway 91, shown being advanced at a face 92. A rotary cutting head 56A is mounted at one end of a displaceable boom 93, attached at its other end to the machine 38A, the latter being mounted on crawler tracks 94. Conventionally, the machine 38A is provided with a pick-up conveyor 95 to discharge mineral detached by the cutting head 56A onto a belt conveyor 96 extending along the roadway 91.

A discharge, exit end 5A of a water powered, ventui ventilator tube 60A (which may be considered equivalent to the hollow shaft 60 of FIGS. 2 to 6) is located in the vicinity of the rotary cutting head 56A, the venturi ventilator 60A in this embodiment being constituted by ventilation ducting extending a considerable length along the roadway 91 and carried for example on a wheeled track or runner system, in turn carried by the conventionally-provided "I"-section, roadway supporting rings 97. The hollow shaft 60A is carried in part by the boom 93 and in part by the rings 97.

Adjacent the discharge, exit end 5A of the venturi ventilator 60A is at least one water spray nozzle 61 connectable to a source of pressurised water to produce water-jet 62, to induce an air flow along the venturi ventilator 60A. As an alternative to air flow being induced by the water jet 62, the venturi ventilator 60A may be provided with a fan 99. This embodiment also illustrates the possibility of positioning the gas detector 1 in a remote location with respect to the mineral cutting machine 38A and, as with the embodiment of FIG. 5, sampling the air entering the inlet end 63 of the venturi ventilator 60A, with electrical leads 98 from the gas detector 1 extending to an alarm circuit and/or to the pilot circuit 90 of the machine 38A and/or to the mine telemetry system etc, whereby the rotaty cutting head 56A is automatically stopped upon an alarm condition being sensed by the gas detector 1.

What we claim is:

1. A gas detector to detect a predetermined gas of interest within an air sample, said detector comprising an air sampling tube; an infra-red radiation source located at one end of said air sampling tube to emit an infra-red radiation beam along said air sampling tube; an infra-red sensor located at the other end of said air sampling tube; an optical filter appropriate to said gas of interest located in said infra-red radiation beam; an air sample inlet located adjacent one end of said air sampling tube and an air sample outlet located adjacent the other end of said air sampling tube; an air flow detector located at said air sample outlet; said gas detector being capable of emitting an electrical signal, or a changed electrical signal, in accordance with whether said gas of interest is or is not detected within said air sampling tube; a pure, reference gas source; valve means to control admission of reference gas from said reference gas source to said air sampling tube at prescribed intervals of time; and a timing device serving to control admission of reference gas to said air sampling tube automatically, at preselected intervals of time, 2. A gas detector as claimed in claim 1, wherein said optical filter is located adjacent said infra-red sensing means.

3. A gas detector as claimed in claim 1, wherein said reference gas is $CO_2$.

4. A gas detector as claimed in claim 1, wherein a cylinder supplies said reference gas at super atmospheric pressure.

5. A gas detector as claimed in claim 4, wherein a reference gas pressure switch is incorporated in a supply line from said cylinder.

6. A gas detector as claimed in claim 1, comprising a valve to control alternatively admission of said air samples or, at said prescribed intervals of time, said reference gas to said air sampling tube.

7. A gas detector as claimed in claim 6, wherein said valve is solenoid operated.

8. A gas detector as claimed in claim 1, comprising air pump means for said air sample.

9. A gas detector as claimed in claim 8, wherein said air pump means is an electrically driven air pump.

10. A gas detector as claimed in claim 1, comprising an air sample inlet, and an air filter located in said air sample inlet.

11. A gas detector as claimed in claim 1 wherein said air flow detector is of the mass flow meter kind.

12. A gas detector as claimed in claim 1, provided with a barometric pressure compensating device generating a pressure compensating electrical signal modifying said gas detector electrical signal to compensate for elevational variation or atmospheric exposure of said gas detector.

13. A mining machine provided with at least one rotary cutting head, and connected to a gas detector to detect a predetermined gas of interest within an air sample, said detector comprising an air sampling tube, an infra-red radiation source located at one end of said air sampling tube to emit an infra-red radiation beam along said air sampling tube, an infra-red sensor located at the other end of said air sampling tube, an optical filter appropriate to said gas of interest located in said infra-red radiation beam, an air sample inlet located adjacent one end of said air sampling tube and an air sample outlet located adjacent the other end of said air sampling tube, an air flow detector located at said air sample outlet, with said gas detector capable of emitting an electrical signal, or a changed electrical signal, in accordance with whether said gas of interest is or is not detected within said air sampling tube, a pure, reference gas source, valve means to control admission of reference gas from said reference gas source to said air sampling tube at prescribed intervals of time, and a timing device serving to control admission of reference gas to said air sampling tube automatically, at preselected levels of time.

14. A mining machine as claimed in claim 13, wherein said gas detector is on board said machine.

15. A mining machine as claimed in claim 13, wherein said gas detector is remote from said machine but connected thereto and to an associated mining telemetry system.

16. A mining machine as claimed in claim 13, of the shearer type.

17. A mining machine as claimed in claim 16, comprising a ranging arm on which said gas detector is mounted.

18. A mining machine as claimed in claim 6, comprising a hollow shaft co-axial with said rotary cutting head, with said gas detector capable of detecting a predetermined gas of interest within an air sample entering said hollow shaft.

19. A mining machine as claimed in claim 13, of the roadheader type.

20. A mining machine as claimed in claim 13, wherein drive to said rotary cutting head is stopped automatically upon an electrical signal, or changed electrical signal, being emitted by said gas detector upon detection of said gas of interest, above a prescribed threshold.

21. A mining machine as claimed in claim 20, wherein drive stoppage is effected by de-clutching a transmission to said rotary cutting head.

22. A mining machine as claimed in claim 13, provided with at least one said gas detector in the vicinity of said rotary cutting head.

23. A mining machine as claimed in claim 13 wherein the gas detector is mounted on said mining machine at an upstream end of said mining machine, with regard to conventional, mine face ventilating air flow direction.

* * * * *